United States Patent [19]

Sugiyama et al.

[11] Patent Number: 5,006,160
[45] Date of Patent: Apr. 9, 1991

[54] IMINO[(3-HALOGENOPHENYL)AMINO]A-CETIC ACID DERIVATIVES AND HERBICIDES CONTAINING SAME

[75] Inventors: Yuichi Sugiyama; Takashi Isono; Yukihiro Nakamura; Akihiro Takaiwa; Kenichi Komatsubara, all of Tokyo, Japan

[73] Assignee: SDS Biotech Kabushiki Kaisha, Japan

[21] Appl. No.: 375,587

[22] Filed: Jul. 5, 1989

[30] Foreign Application Priority Data

Jul. 6, 1988 [JP] Japan .................. 63-166798
Jul. 7, 1988 [JP] Japan .................. 63-167717

[51] Int. Cl.$^5$ .............................. A01N 37/10
[52] U.S. Cl. ................................ 71/111; 71/114; 560/35; 562/440
[58] Field of Search .............. 560/35; 562/440; 71/111, 114

[56] References Cited

U.S. PATENT DOCUMENTS

| | | | |
|---|---|---|---|
| 2,577,900 | 12/1951 | Lisk et al. | 560/35 |
| 4,116,974 | 9/1978 | Forge et al. | 560/35 |
| 4,670,593 | 6/1987 | Teach | 71/114 |

FOREIGN PATENT DOCUMENTS

| | | | |
|---|---|---|---|
| 97107 | 12/1983 | European Pat. Off. | 560/35 |
| 53-108933 | 9/1978 | Japan | 562/440 |

OTHER PUBLICATIONS

Chem. Abst., vol. 97, #197999q (1982).

*Primary Examiner*—James H. Reamer
*Attorney, Agent, or Firm*—Webb, Burden, Ziesenheim & Webb

[57] ABSTRACT

In accordance with the present invention, there are provided novel compounds represented by the following general formula [I], and herbicides containing as their active ingredients.

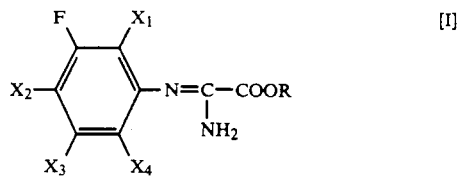

[I]

wherein $X_1$, $X_2$, $X_3$ and $X_4$ are each hydrogen, halogen or methyl, and R is hydrogen or a lower alkyl.

There are also provided herbicides containing as their active ingredients compounds represented by the following general formula [II].

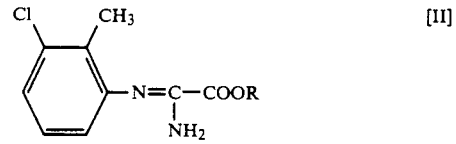

[II]

wherein R is hydrogen or a lower alkyl.

6 Claims, No Drawings

IMINO[(3-HALOGENOPHENYL)AMINO]ACETIC ACID DERIVATIVES AND HERBICIDES CONTAINING SAME

FIELD OF THE INVENTION

This invention relates to novel imino[(3-fluorophenyl)amino]acetic acid derivatives and herbicides containing the derivatives as active ingredients.

In another aspect, the invention relates to herbicides containing imino[(3-chloro-2-methylphenyl)amino]acetic acid derivatives as active ingredients.

BACKGROUND OF THE INVENTION

Heretofore, imino[(substituted or unsubstituted phenyl)amino]acetic acids have been known from such references as Japanese Patent L-O-P Publns. Nos. 589/1963, 14041/1963 and 20197/1964, Japanese Patent Publns. Nos. 10287/1975 and 22018/1975, Japanese Patent L-O-P Publns. Nos. 108933/1978, 88158/1982, 85351/1982, 85352/1982 and 38249/1983, and J. Org. Chem., 43, 4485–4487(1978), but these references fail to disclose imino[(3-fluorophenyl)amino]acetic acid. Further, Japanese Patent L-O-P Publn. No. 88157/1982 discloses imino[(substituted or unsubstituted phenyl)amino]acetic acid esters as reaction intermediates, but it fails to define structures of the esters as isolated and also fails to refer, in concrete, to imino[(3-fluorophenyl)amino]acetic acid derivatives or imino[(3-chloro-2-methylphenyl)amino]acetic acid derivatives. Further, some of the above-mentioned prior art references suggest a possibility that imino[(substituted or unsubstituted phenyl)amino]acetic acids have general herbicidal activities or agricultural activities, but they fail to describe concretely these activities of the acids and hence it can hardly be said that said acids are disclosed as herbicides.

In this connection, any compounds which are considered to be useful as herbicides, particularly those for use in a paddy field, are required to have the following properties.

(i) The compounds have no phytotoxicity to paddy rice,
(ii) said compounds exhibit herbicidal activities to weeds, in particular, water chestnut (Eleocharis kuroguwai) and water nutsedge (Cyperus serotinus).
(iii) said compounds exhibit herbicidal activities even in the treatment of barnyardgrass of the 3-leaf stage.

After extensive researches conducted with the view of obtaining compounds having such properties as mentioned above, we have accomplished the present invention on the basis of our finding that imino[(3-fluorophenyl)amino]acetic acid derivatives, which compounds are novel have excellent herbicidal activities. The invention thus accomplished has been based also on our further finding that imino[(3-chloro-2-methylphenyl)amino]acetic acid derivatives have excellent herbicidal activities.

OBJECT OF THE INVENTION

The present invention has been accomplished in consideration of the prior art as mentioned above, and an object of the invention is to provide compounds which are useful as herbicides, particularly those for use in paddy field, and herbicides containing said compounds as active ingredients.

SUMMARY OF THE INVENTION

The novel compounds of the present invention are represented by the following general formula [I].

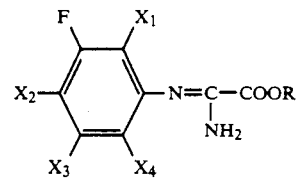

wherein $X_1$, $X_2$, $X_3$ and $X_4$ are each hydrogen, halogen or methyl, and R is hydrogen or a lower alkyl.

The first herbicides of the present invention are characterized by containing the compounds as represented by the general formula [I] as mentioned above.

The second herbicides of the present invention are characterized by containing compounds represented by the following general formula [II] as active ingredients.

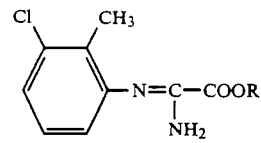

wherein R is hydrogen or a lower alkyl.

DETAILED DESCRIPTION OF THE INVENTION

The novel compounds and herbicides according to the present invention are illustrated below in detail.

The novel compounds of the invention are represented by the following general formula [I] as mentioned previously.

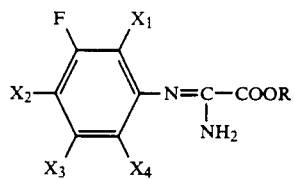

wherein $X_1$, $X_2$, $X_3$ and $X_4$ are each hydrogen, halogen or methyl, and R is hydrogen or a lower alkyl.

In the above formula, the halogen includes chlorine, fluorine and bromine, and the lower alkyl includes methyl, ethyl, n-propyl, i-propyl, n-butyl, i-butyl, sec-butyl, t-butyl, n-amyl and i-amyl.

In this connection, the compounds represented by the above-mentioned general formula [I] may also exist as tautomers represented by the following general formula [I]'. In the present invention, however, the tautomers represented by the general formula [I]' are encompassed by the compounds represented by the general formula [I].

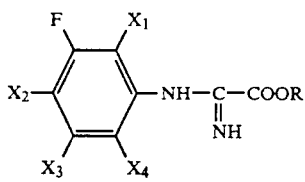

wherein $X_1$ to $X_4$ and R are as defined above.

The compounds as mentioned above may be prepared, for example, by the following reaction routes (in the formulas shown in the reaction routes, $X_1$ to $X_4$ are as defined above, and R' is a lower alkyl).

Route (a)

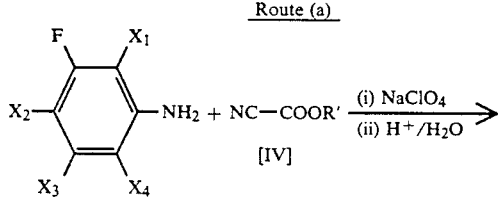

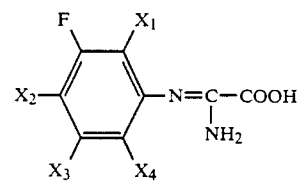

[I] (R = H)

Route (b)

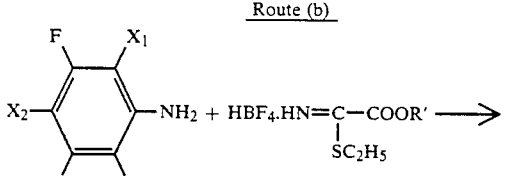

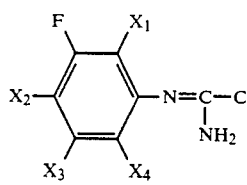

[I] (R = lower alkyl)

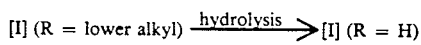

The above-mentioned route (a) is similar to a process disclosed in Japanese Patent L-O-P Publn. No. 108933/1978. The route (b) gives an alkyl ester derivative of the compound of the present invention by reacting the amine of a compound of the general formula [III] with a compound of the general formula [V], followed by neutralization. This alkyl ester derivative is hydrolyzed to an acid of the compound [I] of the present invention in which R is H. The compound of the general formula [V] may be obtained by reacting $H_2NC(S)C(O)OR'$ with Meerwein reagent (triethyloxonium tetrafluoroborate) in methylene chloride.

Typical examples of the compounds [I] of the present invention are those shown in Table 1. Hereinafter, the compounds of the invention mentioned in the specification will be indicated individually by reference to the compound No. designated in Table 1.

The compounds of the invention are designated by way of the symbols in the aforesaid general formula. In the column showing physical properties of compound shown in Table 1, NMR represents a nuclear magnetic resonance spectrum, the solvent used in the measurement is shown in round brackets, and the unit is ppm. IR represents an infrared spectrum and the unit is $cm^{-1}$.

TABLE 1

| | | IR | NMR(CDCl$_3$) |
|---|---|---|---|
| 1 | $X_1$ = H<br>$X_2$ = H<br>$X_3$ = H<br>$X_4$ = H<br>R = H | 3260, 1660<br>1365 | |
| 2 | $X_1$ = H<br>$X_2$ = H<br>$X_3$ = H<br>$X_4$ = H<br>R = CH$_3$ | 3350, 1730<br>1640 | |
| 3 | $X_1$ = H<br>$X_2$ = H<br>$X_3$ = H<br>$X_4$ = H<br>R = C$_2$H$_5$ | 3300, 1730<br>1650 | |
| 4 | $X_1$ = CH$_3$<br>$X_2$ = Br<br>$X_3$ = H<br>$X_4$ = H<br>R = H | 3330, 1680<br>1350 | |
| 5 | $X_1$ = CH$_3$<br>$X_2$ = Br<br>$X_3$ = H<br>$X_4$ = H<br>R = C$_2$H$_5$ | 3480, 3350<br>1740, 1630 | 1.41(t, 3H),<br>2.04(d, 3H),<br>4.30(q, 2H),<br>4.6–5.8(br, 2H),<br>6.1–7.3(m, 2H) |
| 6 | $X_1$ = H<br>$X_2$ = H<br>$X_3$ = H<br>$X_4$ = CH$_3$<br>R = H | 3300, 1665<br>1350 | |
| 7 | $X_1$ = H<br>$X_2$ = H<br>$X_3$ = H<br>$X_4$ = CH$_3$<br>R = C$_2$H$_5$ | 3480, 3370, 1730<br>1650 | 1.36(t, 3H),<br>2.01(s, 3H),<br>4.22(q, 2H),<br>4.6–5.6(br, 2H),<br>6.0–7.1(m, 3H) |
| 8 | $X_1$ = H<br>$X_2$ = H<br>$X_3$ = H<br>$X_4$ = F<br>R = H | 3450, 1630<br>1495, 1325 | |
| 9 | $X_1$ = H<br>$X_2$ = CH$_3$<br>$X_3$ = H<br>$X_4$ = H<br>R = H | 3275, 1665<br>1360 | |
| 10 | $X_1$ = CH$_3$<br>$X_2$ = H<br>$X_3$ = H<br>$X_4$ = H<br>R = H | 3300, 1670<br>1360 | |
| 11 | $X_1$ = CH$_3$<br>$X_2$ = H<br>$X_3$ = H<br>$X_4$ = H | 3350, 1730<br>1640 | |

TABLE 1-continued

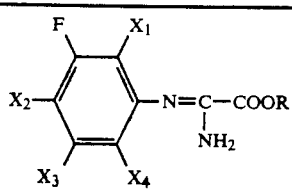

| | | IR | NMR(CDCl₃) |
|---|---|---|---|
| 12 | R = CH₃<br>X₁ = CH₃<br>X₂ = H<br>X₃ = H<br>X₄ = H | 3350, 1730<br>1640 | |
| 13 | R = C₂H₅<br>X₁ = H<br>X₂ = H<br>X₃ = F<br>X₄ = H | 3375, 3270<br>1710, 1640 | 1.42(t, 3H),<br>4.38(q, 2H)<br>4.8-5.8(m),<br>6.1-7.5(m) |
| 14 | R = C₂H₅<br>X₁ = CH₃<br>X₂ = H<br>X₃ = H<br>X₄ = H | 3350, 1730<br>1640 | |
| 15 | R = CH₂—C₆H₅<br>X₁ = CH₃<br>X₂ = H<br>X₃ = H<br>X₄ = CH₃<br>R = H | 3270, 1670<br>1350 | |

The first herbicides of the present invention contain as their active ingredients the compound represented by the general formula [I].

The first herbicides of the present invention which contain as active ingredients the compounds of the general formula [I] exhibit strong herbicidal activities on a wide variety of weeds. The herbicide containing as its active ingredient a compound presented by the general formula [I] wherein $X_1$ is methyl and $X_2$, $X_3$ and $X_4$ are each hydrogen exhibits strongest herbicidal activities. When the herbicides of the invention as mentioned above are applied in an amount of 0.1 to 10 kg per 1 hectare in terms of their active ingredient to weeds immediately before germination thereof or at an initial or middle stage of growth thereof, such a great variety of weeds as will be mentioned later can be exterminated or controlled in the course of about 1-2 weeks after application of said herbicides.

When the amount of the herbicides containing the novel compounds of the invention to be applied to is regulated or an appropriate method of application thereof is adopted, weeds can be selectively controlled in the fields where specific firm products are cultivated such as corn, potato, sugar cane, peanut, soybean, sunflower, barley, wheat, sol gum, paddy rice, cotton and fruit tree. When the present herbicides are applied, in particular, to paddy field, such strong weeds as barnyard grass, bulrush, water chestnut and water nutsedge can be controlled, and said herbicides exhibit their herbicidal effects on barnyard grass even when they are applied to barnyard grass of the 3-leaf stage.

The second herbicides of the present invention are illustrated hereinafter. The present second herbicides contain as their active ingredients the compounds represented by the following general formula [II].

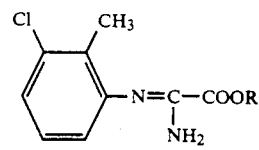

wherein R is hydrogen or a lower alkyl.

The lower alkyl in the above formula includes such groups as mentioned previously.

The compounds of the general formula [II] may also exist as tautomers represented by the following general formula [II]'. In the present specification, the tautomers of the general formula [II] are construed to be encompassed by the compounds of the general formula [II].

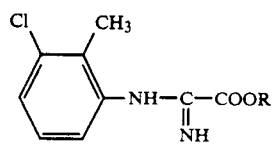

wherein R is as defined above.

The compounds of the general formula [II] may be prepared by the procedure similar to that employed in the case of the compounds of the general formula [I], for example, by the following reaction routes.

Route (a)

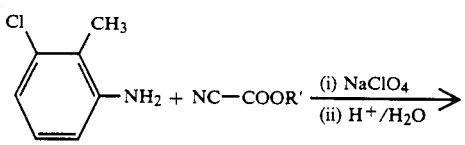

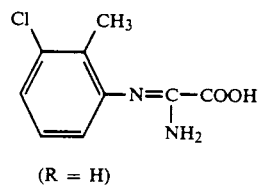

(R = H)

Route (b)

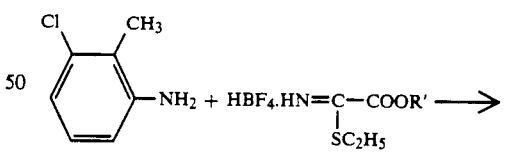

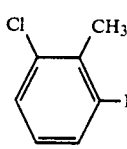

(R' = lower alkyl)

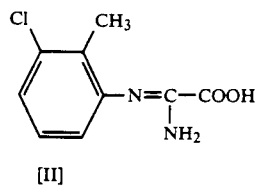

Typical examples of the compounds of the general formula [II] of the present invention are those shown in Table 2.

TABLE 2

| Compound No. | R |
|---|---|
| 16 | H |
| 17 | $CH_3$ |
| 18 | $C_2H_5$ |

The second herbicides of the present invention which contain as their active ingredients the above-mentioned compounds of the general formula [II] exhibit excellent herbicidal activities in the same manner as in the first herbicides of the invention.

The herbicides of the present invention may be obtained by formulating the above-mentioned compounds of the general formula [I] or [II], together with solid or liquid carriers, according to the conventional method of the formulation of agricultural chemicals, into various types of formulations, for example, emulsions, wettable powders, dusts, granules, flowables, etc. In that case, there may be mixed therewith, if necessary, various additives, such as emulsifiers and spreaders, for the purposes intended, and various kinds of surfactants for other purposes and, in addition thereto, other herbicides or agricultural chemicals, for example, insecticides, germicides, nematicides, plant growth regulators, fertilizers, etc., for the purpose of expanding an effective range of the present herbicides.

The herbicides of the invention may be used for controlling a wide variety of weeds, for example, those as exemplified below. That is, such weeds include broad-leaved weeds, for example, *Stellaria media, Chenopodium album, Sagina japonica, Chenopodium ficifolium, Polygonum nodosum, Portulaca oleracea, Capsella bursapastoris, Lepidium virginicum, Rorippa indica, Cardamine flexuosa, Abutilon theophrasti, Sida spinosa, Ipomoea purpurea, Senecio vulgaris, Sonchus asper, Bidens frondosa, Ambrosia artemisiaefolia, Aster subulatus, Lamium amplexicaule, Oxalis corniculata, Amaranthus retroflexus, Vicia sativa, Galium aparine, Solanum nigrum, Datura stramonium* and the like; grasses of Gramineae, for example, *Poa annua, Alopecurus aequalis, Digitaria adscendens, Eleusine indica, Setaria viridis, Echinochloa crus-galli, Agropyron Kamoji, Lolium perenne, Bromus unioloides, Avena fatua, Polypogon Higegaweri, Panicum dichotomiflorum* and the like; and weeds of Cyperaceae, for example, *Cyperus microiria, Cyperus Iria, Cyperus serotinus, Eleocharis kuroguwai, Eleocharis acicularis* and the like.

The present invention is illustrated below with reference to examples, but it should be construed that the invention is in no way limited to those examples.

First, the processes for preparing the novel compounds of the invention are illustrated hereinafter.

PREPARATIVE EXAMPLE 1

Compound No. 10

To 1/10N acetic acid solution of perchloric acid (2.0 mmol, 20 ml) were added 3-fluoro-2-methylaniline hydrochloride (20 mmol, 3.2 g), ethyl cyanoformate (20 mmol, 2.0 g) and sodium perchlorate (6.0 mmol, 0.73 g), and the mixture was heated at 100° C. for 1 hour. After having been cooled, the mixture was incorporated with 6N hydrochloric acid (40 ml), followed by heating at 100° C. for one hour. The reaction mixture was concentrated under reduced pressure, and the resulting mixture was then mixed with water (40 ml) and ethyl acetate (30 ml), followed by neutralization with sodium bicarbonate. The mixture thus treated was allowed to stand, and white powder formed was collected by filtration, followed by washing with water and ethanol. Recrystallization from methanol gave colorless crystal (5.1 mmol, 1.0 mg). The yield was 26%.

PREPARATIVE EXAMPLE 2

Compound No. 10

To a methylene chloride solution (200 ml) of ethyl imino(ethylthio)acetate hydrogentetrafluoroborate (400 mmol) was added a methylene chloride solution (100 ml) of 3-fluoro-2-methylaniline (400 mmol, 50 g), and the mixture was thoroughly mixed and allowed to stand at room temperature overnight. The reaction mixture was incorporated with n-hexane (600 ml), thoroughly mixed and allowed to stand for 2 hours. The supernatant liquid of the reaction mixture was removed by decantation, and the resulting reaction mixture was incorporated with methylene chloride (300 ml), followed by neutralization with addition of an aqueous sodium bicarbonate solution with thorough stirring. The resulting methylene chloride solution was concentrated under reduced pressure, incorporated with 3N hydrochloric acid (400 mol) and ethanol (200 ml), and the mixture was thoroughly shaked while heating at 60° C. The reaction mixture was concentrated under reduced pressure, and the resulting concentrate was incorporated with water (300 ml) and thoroughly stirred by shaking. To the resulting mixture was added an aqueous sodium bicarbonate solution, and white powder formed was collected by filtration, followed by rinsing with water and ethanol. Recrystallization from 2N hydrochloric acid gave white crystal (190 mmol, 37 g). The yield was 48%.

PREPARATIVE EXAMPLE 3

Compound No. 5

A mixture of a methylene chloride solution (25 ml) of 4-bromo-3-fluoro-2-methylaniline (60 mmol, 12 g) and a methylene chloride solution (25 ml) of ethyl imino(ethylthio)acetate hydrogentetrafluoroborate (60 mmol) was stirred at room temperature for 5 hours, and allowed to stand overnight, followed by rinsing twice with a cold 5% aqueous sodium bicarbonate solution. The methylene chloride solution was dried over Glauber's salt followed by passing through a silica gel (Wacogel C-200) column, and the eluate was concentrated under reduced pressure to obtain 15 g of crude crystal. Recrystallization from methylene chloride n-hexane gave white crystal (43 mmol, 13 g). The yield was 72%.

PREPARATIVE EXAMPLE 4

Compound No. 4

To a solution of ethyl imino[(4-bromo-3-fluoro-2-methylphenyl)amino]acetate (6.6 mmol, 2.0 g) in methanol (20 ml) was added 2N sodium hydroxide (4 ml), and the resulting mixture was heated at 60° C. and stirred for 10 minutes. The methanol was ditilled off under reduced pressure, and the residue was neutralized with 2N hydrochloric acid while cooling with ice. The precipitate formed was collected by filtration, followed by rinsing with water and n-hexane. Recrystallization from methanol gave a transparent plate crystal (2.9 mmol, 0.80 g). The yield was 44%.

PREPARATIVE EXAMPLE 5

Compound No. 16

The title compound was prepared according to an example disclosed in Japanese Patent L-O-P Publn. No. 108983/1983. The yield was 43%. Decomposition point was 148° C.

PREPARATIVE EXAMPLE 6

Compound No. 18

To a solution of 3-chloro-2-methylaniline (60 mmol) in dried dichloroethane (25 ml) was added dropwise with stirring at room temperature over a period of 20 minutes a solution of dried dichloroethane (25 ml) containing ethyl imino(ethylthio)acetate hydrogentetrafluoride (50 mmol). After the dropwise addition, the mixture was stirred for 5 hours and allowed to stand over night. After having been washed with a cooled 5% aqueous sodium hydrogencarbonate solution and water in that order, followed by drying over anhydrous sodium sulfate, the reaction mixture was treated by silica gel (Wacogel C-200) column chromatography to give the compound No. 18 as a syrup-like substance. The yield was 91.0%. Infrared spectroscopic spectrum: 3550, 1730, 1635 cm$^{-1}$. The values of elementary analysis as found were ±0.3% of the calculated values.

Set forth below are formulation examples of the herbicides of the present invention, wherein parts are by weight.

EXAMPLE 1

Wettable

A wettable containing 50% by weight of an active ingredient compound was prepared by mixing and pulverizing 50 parts of a compound shown in Table 1 or 2 as an active ingredient, 35 parts of talc, 5 parts of diatomaceous earth, 5 parts of white carbon and 5 parts of polyoxyetylene alkylallyl ether.

EXAMPLE 2

Granule

A granule containing 10% by weight of an active ingredient was prepared by adding about 20 parts of water to a mixture comprising 10 parts of a compound shown in Table 1 or 2 as an active ingredient, 30 parts of bentonite, 58 part of talc and 2 parts of polyoxyethylene alkylallyl ether, kneading the resulting mixture, granulating the kneadate, and drying the resulting granules, followed by screening.

In order to demonstrate herbicidal effects of the herbicides of the present invention, some of typical test examples are given below. In the test examples, herbicidal effects and phytotoxicities of the herbides used were visually observed, and the results were represented by a 11-point grading wherein 0 signifies no herbicidal effect or phytotoxicity and 10 signifies complete withering.

TEST EXAMPLE 1

Flooded soil treatment (before germination of weeds)

A pot having an area of 80 cm$^2$ is filled with a paddy soil and sowed at a surface layer of about 2 cm with seeds of barnyardgrass (*Echinochloa crus-galli*), ammania (*Ammania multiflora*) and bulrush(*Scirpus juncoides*), and a tuber of water nutsedge(*Cyperus serotinus*) and a paddy rice of the 2-leaf stage were transplanted in two places, respectively, of the pot, wherein water was maintained at the depth of 3 cm. One day after, a wettable containing the compound of the present invention prepared in accordance with the procedure of Example 1 was applied into water. Three weeks after the application of the herbicide, herbicidal effects and phytotoxicity to the paddy rice were visually observed to obtain the results as shown in Table 3.

TEST EXAMPLE 2

Flooded soil treatment (after germination of weeds)

Test example 1 was repeated with the exception that the weeds and paddy rice were allowed to grow at room temperature for 10 days before the application of the herbicide. The results obtained are as shown in Table 4.

TABLE 3

| Compound No. | Amount of herbicide applied a.i.kg/ha | Herbicidal effect | | | | phytotoxicity to paddy rice |
|---|---|---|---|---|---|---|
| | | Barnyard grass | Ammania | Bulrush | Water nutsedge | |
| 1 | 4 | 10 | 8 | 6 | 8 | 2 |
| 2 | 4 | 10 | 8 | 6 | 7 | 0 |
| 3 | 4 | 10 | 10 | 7 | 8 | 2 |
| 4 | 4 | 8 | 6 | 2 | 6 | 0 |
| 5 | 4 | 8 | 5 | 3 | 6 | 0 |
| 6 | 4 | 10 | 10 | 10 | 8 | 0 |
| 7 | 4 | 8 | | | | 0 |
| 8 | 4 | 8 | | | | 0 |
| 9 | 4 | 7 | | | | 0 |
| 10 | 4 | 10 | 10 | 10 | 10 | 2 |
| | 1 | 10 | 10 | 9 | 10 | 0 |
| | 0.5 | 10 | 8 | 9 | 9 | 0 |
| 12 | 4 | 8 | 8 | 8 | 10 | 3 |
| 13 | 4 | 9 | 6 | 4 | 3 | 0 |
| 14 | 4 | 7 | | | | |
| 15 | 4 | 10 | 10 | 5 | 4 | 0 |

TABLE 4

| Compound No. | Amount of herbicide applied a.i.kg/ha | Herbicidal effect | | | | phytotoxicity to paddy rice |
|---|---|---|---|---|---|---|
| | | Barnyard grass | Ammania | Bulrush | Water nutsedge | |
| 1 | 4 | 6 | 5 | 5 | 3 | 0 |
| 3 | 4 | 6 | 5 | 6 | 3 | 0 |
| 6 | 4 | 5 | 8 | 10 | 8 | 0 |
| 10 | 4 | 10 | 10 | 10 | 10 | 0 |
| | 1 | 10 | 8 | 10 | 10 | 0 |
| 12 | 4 | 9 | 8 | 7 | 10 | 0 |
| 13 | 4 | 8 | 3 | 0 | 0 | 0 |

TEST EXAMPLE 3

Flooded soil treatment (before germination of weeds)

A pot having an area of 80 cm² was filled with a paddy soil and sowed at the surface layer of about 2 cm with seeds of barnyard grass (*Echinochloa crus-galli*) and bulrush(*Scirpus juncoides*), and a tuber of water nutsedge (*Cyperus serotinus*) and a paddy rice of the 2-leaf stage were transplanted at two places, respectively, of the pot, wherein water was maintained at the depth of 3 cm. One day after, a wettable containing a compound of the present invention prepared in accordance with the procedure of Example 1 was applied into water. Three weeks after the application of the herbicide, herbicidal effects and phytotoxicity to the paddy rice were visually observed to obtain the results as shown in Table 5. As a control herbicide, Prechilachlor is used.

TEST EXAMPLE 4

Flooded soil treatment (after germination of weeds)

Test Example 3 was repeated with the exception that the weeds and paddy rice were allowed to grow at room temperature for 10 days before the application of the herbicide. The results obtained are as shown in Table 6. As a control herbicide, Prechilachlor is used.

TABLE 5

| Compound No. | Amount of herbicide applied a.i.kg/ha | Herbicidal effect | | | phytotoxicity to paddy rice |
|---|---|---|---|---|---|
| | | Barnyard grass | Bulrush | Water nutsedge | |
| 16 | 8 | 10 | 10 | 10 | 3 |
| | 4 | 10 | 10 | 10 | 2 |
| 17 | 8 | 10 | 10 | 10 | 3 |
| | 4 | 10 | 10 | 10 | 2 |
| 18 | 8 | 10 | 10 | 10 | 2 |
| | 4 | 10 | 10 | 10 | 2 |
| Prechilachlor | 4 | 10 | 10 | 10 | 5 |

TABLE 6

| Compound No. | Amount of herbicide applied a.i.kg/ha | Herbicidal effect | | | phytotoxicity to paddy rice |
|---|---|---|---|---|---|
| | | Barnyard grass | Bulrush | Water nutsedge | |
| 16 | 8 | 10 | 10 | 10 | 0 |
| | 4 | 10 | 9 | 10 | 0 |
| 17 | 8 | 10 | 10 | 10 | 0 |
| | 4 | 10 | 8 | 10 | 0 |
| 18 | 8 | 10 | 10 | 10 | 0 |
| | 4 | 10 | 7 | 10 | 0 |
| Prechilachlor | 4 | 9 | 9 | 5 | 3 |

What is claimed is:

1. A compound represented by the general formula

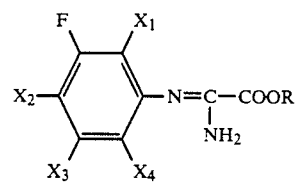

wherein $X_1$, $X_2$, $X_3$ and $X_4$ are each hydrogen, halogen or methyl, and R is hydrogen or a lower alkyl.

2. The compound as claimed in claim 1 wherein:
   (a) $X_1$ is methyl;
   (b) $X_2$, $X_3$, and $X_4$ are each hydrogen or methyl; and
   (c) R is hydrogen, methyl or ethyl.

3. A herbicide containing as its active ingredient a compound represented by the following general formula

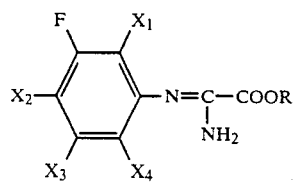

wherein $X_1$, $X_2$, $X_3$ and $X_4$ are each hydrogen, halogen or methyl, and R is hydrogen or a lower alkyl.

4. The herbicide as claimed in claim 3 wherein said herbicide contains a compound of the general formula wherein:

(a) $X_1$ is methyl;

(b) $X_2$, $X_3$, and $X_4$ are each hydrogen or methyl; and (c) R is hydrogen, methyl or ethyl.

5. A herbicide containing as its active ingredient a compound represented by the following general formula

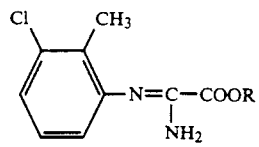

[II]

wherein R is hydrogen or a lower alkyl.

6. The herbicide as claimed in claim 5 wherein said herbicide contains a compound of the general formula wherein R is hydrogen, methyl or ethyl.

* * * * *